United States Patent [19]

Lin

[11] Patent Number: 5,223,630
[45] Date of Patent: Jun. 29, 1993

[54] GLYCOLIDE PURIFICATION PROCESS

[75] Inventor: Kang Lin, Newark, Del.

[73] Assignee: E. I. Du Pont de Nemours and Company, Wilmington, Del.

[21] Appl. No.: 709,175

[22] Filed: Jun. 3, 1991

Related U.S. Application Data

[63] Continuation of Ser. No. 418,834, Oct. 10, 1989, abandoned.

[51] Int. Cl.$^5$ .......................................... C07D 319/06
[52] U.S. Cl. .................................................... 549/274
[58] Field of Search ........................................ 549/274

[56] References Cited

U.S. PATENT DOCUMENTS

| | | | |
|---|---|---|---|
| 1,095,205 | 5/1914 | Gruter et al. | 549/274 |
| 3,435,008 | 8/1969 | Schmitt et al. | 549/274 |
| 3,442,871 | 5/1969 | Schmitt et al. | 549/274 |
| 3,457,280 | 7/1969 | Schmitt et al. | 549/274 |
| 3,597,470 | 8/1971 | Schmitt et al. | 549/274 |
| 4,650,851 | 3/1987 | Rhum et al. | 549/274 |
| 4,835,293 | 5/1989 | Bhatia | 549/274 |

FOREIGN PATENT DOCUMENTS 148777 8/1984 Japan .................................. 549/274

OTHER PUBLICATIONS

*Chemical Abstracts* 102:95658g, "Purification of glycolide," abstract of Japan patent application 59-148,777 (1985).

Saunders, et al., "Introduction into Organic Laboratory Techniques," 2nd ed., Saunder Publishing Co., pp. 481-488 (1982).

*Primary Examiner*—Glennon H. Hollrah
*Assistant Examiner*—Mark W. Russell

[57] ABSTRACT

A process for preparing suture-grade $\beta$-glycolide by purifying crude glycolide which comprises contacting the crude glycolide with a primary solvent which will dissolve the crude glycolide and residual impurities without dissolving primary impurities; removing the primary impurities; recovering the glycolide and residual impurities by evaporating the primary solvent at a temperature below 42° C.; removing residual impurities by washing the glycolide with a washing solvent in which the residual impurities are soluble; and isolating the $\beta$-glycolide crystals which remain.

10 Claims, No Drawings

GLYCOLIDE PURIFICATION PROCESS

CROSS REFERENCE TO RELATED APPLICATION

This is a continuation of application Ser. No. 07/418,834, filed Oct. 10, 1989 now abandoned.

BACKGROUND OF THE INVENTION

The present invention relates to an improved process for preparing suture grade β-glycolide, and, more particularly, to a process for purifying crude glycolide to a degree of purity required for use as a precursor of biologically absorbably, i.e., resorbable, surgical sutures. The product of the process is crystalline β-glycolide which can be polymerized to polyglycolic acid, a material from which the sutures are fabricated.

Surgical sutures made from absorbable synthetic polymers have been developed as a replacement for "catgut" sutures which are produced from collagenous tissues of animals. Due to biological variations in these tissues, the "catgut" sutures produced from them can have inconsistencies in texture, uniformity of size, strength and rate of absorption into bodily fluids.

To be used as an alternative surgical suture, the synthetic polymers must be capable of being formed, i.e., extruded, into a fiber which is strong, easy to handle, non-toxic and which has uniform and predictable absorptive characteristics. One material which exhibits such characteristics is polyglycolic acid (PGA) of the chemical formula (I)

where n is 350–2400.

Among several methods by which PGA can be prepared, one route involves the polymerization of glycolide (II),

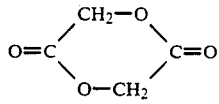

Glycolide, the cyclic dimeric condensation product formed by dehydrating glycolic acid, is ordinarily converted to PGA by a reaction in which the ring is broken, followed by straight-chain polymerization. Such a process is described in by Schmitt et al., U.S. Pat. No. 3,442,871, and according to which, glycolide is heated in the presence of both an alcohol which functions as an initiator and stannous chloride dihydrate which serves as a catalyst.

For use as an effective surgical suture, PGA must retain its strength long enough for the wound to heal before substantial absorption occurs. PGA having an inherent viscosity in the range of from about 1.0 to about 1.6 possesses the desired characteristics for use as a surgical suture, e.g., strength, handleability, non-toxicity, uniform and predictable absorbability. Inherent viscosity is a property applicable to polymers in solution. A capillary viscometer is used to measure inherent viscosity and is calculated using the following formula:

*Inherent Viscosity* $= [\ln(t/t_0)]/c$ wherein t = efflux time of the polymer solution;
$t_0$ = efflux time of the pure solvent;
c = concentration of glycolide in solution, expressed in grams/100 ml.

The term "suture-grade PGA" is used herein to mean PGA having an inherent viscosity in the range of about 1.0 to 1.6 and "suture-grade glycolide" designates a glycolide capable of being polymerized to yield suture-grade PGA. The term "crude glycolide" is used herein to mean any glycolide which is not of suture-grade quality.

To obtain suture-grade PGA, the glycolide from which the PGA is made must be of high purity. Commercially available glycolide ordinarily contains several trace contaminants and typically will yield PGA which has an inherent viscosity of less than 1.0, and this low of an inherent viscosity is unacceptable. Among the impurities in commercial glycolide are free glycolic acid, oligomers of glycolic acid, colorants and free water.

In its solid state, glycolide can exist in two polymorphic forms: α-glycolide and β-glycolide. These two forms of glycolide are discussed in further detail by Schmitt et al. and in U.S. Pat. Nos. 3,435,008 and 3,457,280. Pure α-glycolide is of orthorhombic structure and appears as thin flakes, while β-glycolide is monoclinic in structure and is present as larger, more massive particles.

A more specific distinction between the two polymorphic species is exhibited in their optical characteristics as compared by Schmitt et al.:

|  |  | α-glycolide | β-glycolide |
|---|---|---|---|
| Refractive Indices: | α | 1.486 | 1.430 |
|  | β | 1.506 | 1.552 |
|  | ν | 1.620 | 1.568 |
| Optic Axial Angle: | 2V | 47° 40' | 37° 20' |

Schmitt et al. also disclose that, in the presence of atmospheric moisture, β-glycolide will partially hydrolyze to a material which is then capable of initiating polymerization of the glycolide, i.e., there is no need for a potentially contaminating catalyst. In contrast, α-glycolide is generally inert to atmospheric moisture, and, thus, a catalyst is required to promote its polymerization.

In isolating either of these forms of glycolide, temperature can be a critical factor during formation of the crystals and their subsequent storage. As a rule, glycolide which is precipitated at temperatures below 42° C. is of the β-form, while at temperatures above 42° C. the α-form is generated.

Several methods for purifying and isolating glycolide have been described in the prior art. U.S. Pat. No. 4,650,851, for example, describes a process purifying glycolide in which impure glycolide is dissolved in an organic solvent, such as methylene chloride or tetrahydrofuran. Alumina is then added to the solution forming a slurry in which the dissolved glycolide is in intimate contact with the alumina. Unless the alumina treatment is carried out under carefully controlled conditions, the desired degree of purification will not be achieved. After the slurry has been stirred for up to one hour, the alumina is filtered from the solution. The solvent is then evaporated, leaving purified glycolide.

U.S. Pat. No. 3,457,280 describes methods for isolating α-glycolide by which substantially pure α-glycolide can be obtained from either mixtures of α- and β-glycolide or from substantially pure β-isomer via either of two methods. According to one technique, the source glycolide is dissolved in an inert solvent and heated to a temperature above the transition temperature of 42° C. Suitable solvents include hydroxyl-containing compounds such as n-propanol, n-butanol, isoamyl alcohol, hexanol, ethylene glycol and the like. The α-glycolide is obtained by recrystallization from the solvent at temperatures in excess of 42° C. The α-glycolide can also be isolated by heating the glycolide source in a solid form to a temperature above the transition temperature.

U.S. Pat. No. 3,435,008 describes isolating substantially pure crystalline β-glycolide from either mixtures of α- and β-glycolide or from the substantially pure α-isomer via either of two methods. In one process the substrate is dissolved in an inert solvent, such as n-propanol, n-butanol, isoamyl alcohol, hexanol, ethylene glycol, and this solution is maintained below the transition temperature of 42° C. Also described is a process for polymerizing the β-glycolide to polyglycolic acid in the presence of atmospheric moisture. The use of PGA in surgical sutures is not described.

Japanese Pat. No. 59/148777 (Takayanagi et al.) describes a process for the purification of glycolide in which the glycolide is heated to a molten state and then added dropwise to a solvent such as ethyl acetate, chloroform, or isopropanol, which is maintained between 10° C. and its boiling point. Upon addition to the solvent, some glycolide precipitates and forms a suspension which is then cooled to 20° C. while being stirred, thus precipitating the remaining glycolide. The resulting slurry is filtered and separated using conventional methods and, if necessary, the glycolide may be washed with solvent, filtered and dried under reduced pressure.

In another process described in U.S. Pat. No. 3,763,190, glycolide is prepared in highly pure form from O-haloacetylglycolic acid salts by elimination of a mineral acid salt and attendant closure of the ring. The compound O-chloroacetylglycolic acid is converted to a salt and glycolide is then formed as the salt is heated in a vacuum-sublimation apparatus in which the glycolide condenses on a cool surface.

The present invention provides a convenient method for purifying crude glycolide in yields of 85% or higher, and the β-glycolide which results is suture-grade glycolide, i.e., it can be polymerized to PGA which has an inherent viscosity greater than 1.0.

SUMMARY OF THE INVENTION

The present invention is an improved process for purifying crude glycolide to yield suture-grade β-glycolide. The process comprises the following steps:

(a) contacting crude glycolide with a primary solvent which will dissolve the glycolide and residual impurities which typically include lower molecular weight oligomers of glycolic acid and undesirable colorants without dissolving primary impurities which typically include polyglycolic acid and oligomers of glycolic acid;

(b) removing said insoluble impurities from the resulting solution;

(c) recovering the glycolide and residual impurities by evaporating the primary solvent while maintaining the temperature of the solution below 42° C.;

(d) removing said residual impurities by washing the glycolide with a washing solvent in which said impurities are soluble; and (e) isolating the β-glycolide crystals which remain. Alternatively, in a preferred embodiment, steps (c) and (d) are performed substantially simultaneously by solvent exchange.

DETAILED DESCRIPTION OF THE INVENTION

The process of the invention is applicable to any crude glycolide, such as, for example, commercially produced glycolides which are known to polymerize to polyglycolic acid which has an inherent viscosity below 1.0, and most typically between 0.2 and 0.9.

In Step (a) of the present invention, crude glycolide is brought into contact with a solvent which is capable of dissolving the glycolide and residual impurities but incapable of dissolving certain substances that may be present as primary impurities in the crude glycolide. Among such impurities are polyglycolic acid and some oligomers of glycolic acid. Primary solvents suitable for this purpose are acetone, methyl chloride, chloroform, acetonitrile and tetrahydrofuran. Acetone is the preferred solvent because the glycolide dissolves 33.9% by weight at 23° C. and the acetone does not react with glycolide at room temperature.

During this first step, the solution is maintained at a temperature which allows adequate solubilization of the glycolide but which is below the boiling point of the solvent at a given pressure. Subject to those constraints, the temperature should be as low as possible to minimize the occurrence of reactions which form impurities. For acetone, the temperature of solution should be held between 20° C. and 30° C.

For best results, the solution should contain from about 0.2 to about 25 parts solvent per part of crude glycolide by weight. In a preferred embodiment using acetone as the solvent, from 2.0 to 2.5 parts of acetone are present per part of crude glycolide.

In Step (b), primary impurities which are insoluble in the solvent can be removed from the solution by any convenient separation technique for liquid/solid separation, such as, for example, filtration and centrifugation.

Step (c) comprises separating the solvent from the dissolved material by evaporating the solvent from the solution. During this procedure, the solution must be maintained at a temperature below 42° C. to insure that the glycolide emerging from the solution is the β-form. Preferably, evaporation of the solvent is accomplished at a temperature in the range of from 5°-25° C.

In instances where such temperatures are below the standard boiling point of the solvent being used, the solvent can be removed from the solution by any method which promotes vaporization of the solvent at those temperatures. A preferred method involves applying vacuum to the system which will allow the solvent to boil. In another preferred method, a dry inert gas, such as nitrogen, can be passed through the solution to remove the solvent.

The procedure of regenerating glycolide crystals by evaporation is to be distinguished from the process of recrystallization which has been employed in the art as a common method of purifying glycolide. According to the present invention, evaporating the solvent allows a greater amount of glycolide to be recovered for subsequent treatment in the final step of the process.

Past recrystallization schemes have been operated at temperatures as low as −20° C. to improve yields. Such temperatures, however, can result in the glycolide crystals retaining an unacceptably high amount of moisture which can negatively affect the quality of the PGA produced therefrom. The present invention is operated at no less than 5° C. and can yield drier crystals than those obtained from conventional recrystallization schemes.

Step (d) of the process involves washing the solid material obtained in the preceding step, i.e., the glycolide which remains, with a solvent in which the residual impurities are soluble. Among the residual impurities emerging from solution along with the β-glycolide in this step are lower molecular weight oligomers of glycolic acid and undesirable yellow colorants. The solvent used as a washing agent must be capable of dissolving the solid impurities which are present without dissolving glycolide to a significant extent, i.e., without dissolving more than about 14% of the glycolide. The preferred solvent for this purpose is ethyl acetate.

In the practical application of the invention, Steps (c) and (d) are performed substantially simultaneously by way of a method known as solvent exchange. As the primary solvent is evaporated from the solution under vacuum at a temperature below 42° C., the washing solvent is added to the system. Consequently, the amount of primary solvent in the medium continually decreases, causing formation of β-glycolide crystals, while the amount of washing solvent is increased, and this serves as a wash for the newly formed crystals. Solvent exchange as described may be performed as a batch operation or as a continuous, staged process.

Step (e) involves isolating the dry, newly formed β-glycolide crystals by removing the washing solvent. Most of the washing solvent can be removed by any means of liquid/solid separation, such as filtration or centrifugation. The crystals can then be dried under vacuum at a temperature in the range of 20°-30° C. but preferably at ambient temperatures within that range for convenience.

The invention is illustrated further in the following examples.

EXAMPLE 1

This Example employs the process of the present invention in the purification of glycolide. 50 g of crude glycolide, prepared as described by K. Bhatia in U.S. Pat. No. 4,835,293, was dissolved in 100 g of acetone and agitated for 1 hour at room temperature. Following addition of 1.0 g of "Supercel" filter aid, the solution was filtered. Insoluble materials, i.e., primary impurities in the solution amounted to 0.6 g. Using a rotary evaporator with an ice bath, the solvent was evaporated from the filtrate under a pressure of 33 mm Hg. The 51.3 g of residue, containing a small amount of acetone, was mixed with 50 g of ethyl acetate, forming a slurry. The slurry was stirred at room temperature for 1 hour and cooled to 5° C. in a refrigerator overnight. After the slurry was filtered, 25 g of ethyl acetate at 5° C. was used to wash the resulting filter cake. Upon drying, the cake weighted 41.3 g for a yield of 83%. In addition, the dried glycolide had an acidity of 0.03%. PGA polymer, prepared from this glycolide according to the procedure detailed in Example 1 of U.S. Pat. No. 3,442,871, the teachings of which are incorporated herein by reference, had an inherent viscosity of 1.1 dl/g as a solution of 0.1 g/100 ml in hexafluoroisopropanol at 30° C.

For comparison, a sample of 50 g of the above crude glycolide was dissolved in 75 g of acetone at 50° C. One g of "Supercel" filter aid was added and the solution was filtered. The filtrate was cooled to −20° C. causing some of the glycolide to recrystallize. The solid glycolide was collected by filtration and washed with 34 g of cold (−20° C.) acetone. Following drying, the product weighed 26.1 g for a 52% yield, and had an acidity of 0.03%. PGA polymer produced from this glycolide had an inherent viscosity of 0.97 dl/g.

EXAMPLE 2

The glycolide substrate used in the following Example was a product from a previous acetone recrystallization of crude glycolide. This recrystallized glycolide was still classified as crude, however, since it yielded PGA with an inherent viscosity Of 0.87 dl/g.

First, the present invention, conducted in a manner similar to the procedure of Example 1, was used to purify this crude glycolide, and β-glycolide was recovered in 84% yield which produced PGA with an inherent viscosity of 1.1 dl/g.

For comparison, acetone recrystallization, performed in the manner described in Example 1, gave only 50% recovery of the glycolide. The glycolide product was still not suture-grade because the PGA produced from it had an inherent viscosity of 0.90 dl/g.

EXAMPLE 3

A sample of crude glycolide, of which 10% was insoluble in acetone, was purified by the method of the present invention. In two purification samples, glycolide was obtained in yields of 54% and 65% and produced PGA with inherent viscosities of 1.11 and 1.15 dl/g, respectively.

I claim:
1. A process for preparing suture-grade beta-glycolide which comprises:
   (a) contacting crude glycolide with a primary solvent which will dissolve the glycolide without dissolving primary impurities of polyglycolic acid and oligomers of glycolic acid; to form a solution of glycolide in said primary solvent,
   (b) recovering beta-glycolide by evaporating the primary solvent while maintaining the temperature of the solution below 42° C.; and
   (c) washing the beta-glycolide with a washing solvent to isolate beta-glycolide crystals.
2. The process of claim 1 in which the crude glycolide is contacted with a primary solvent selected from the group consisting of acetone, methylene chloride, chloroform, acetonitrile and tetrahydrofuran to form a solution which contains from about 0.2 to about 25 parts solvent per part of crude glycolide by weight.
3. The process of claim 1 in which the primary solvent is acetone.
4. The process of claim 1 in which the beta-glycolide is recovered by evaporating the primary solvent while maintaining the temperature of the solution in the range of from about 5° to 25° C.
5. The process of claim 1 in which the washing solvent is ethyl acetate.
6. The process of claim 1 in which the beta-glycolide is recovered and washed substantially simultaneously by solvent exchange.
7. An improved process for preparing suture-grade β-glycolide which comprises:
   (a) contacting crude glycolide with a primary solvent which will dissolve the glycolide without dissolving primary impurities of polyglycolic acid and oligomers of glycolic acid to form a solution of glyoclide in said primary solvent; and

(b) recovering β-glycolide by evaporating the primary solvent while maintaining the temperature of the solution below 42° C.

8. The process of claim 7 in which the crude glycolide is contacted with a primary solvent selected from the group consisting of acetone, methylene chloride, chloroform, acetonitrile and tetrahydrofuran to form a solution which contains from 0.2 to about 25 parts solvent per part of crude glycolide by weight.

9. The process of claim 7 in which the primary solvent is acetone.

10. The process of claim 7 in which the β-glycolide is recovered by evaporating the primary solvent while maintaining the temperature of the solution in the range of from about 5° to 25° C.

* * * * *